United States Patent [19]

Riedlinger et al.

[11] Patent Number: 4,805,622

[45] Date of Patent: Feb. 21, 1989

[54] DIRECTION-FINDING SYSTEM FOR LOCALIZATION OF REFLECTION-CAUSING NTERFACES IN THE HUMAN BODY

[76] Inventors: Rainer Riedlinger, Bernhardtstr. 7, 7500 Karlsruhe 1; Friedrich Ueberle, Goethestrasse 62, 6901 Dossenheim, both of Fed. Rep. of Germany

[21] Appl. No.: 25,510

[22] Filed: Mar. 13, 1987

[30] Foreign Application Priority Data

Apr. 10, 1986 [DE] Fed. Rep. of Germany ....... 3612151

[51] Int. Cl.$^4$ ............................................. A61B 10/00
[52] U.S. Cl. ................................. 128/660.06; 367/116
[58] Field of Search .................................. 128/660–661, 128/663, 24 A, 328; 73/602, 597–598, 610–612, 614, 618; 367/7, 99, 104, 112, 116, 120, 124

[56] References Cited

U.S. PATENT DOCUMENTS

| | | | |
|---|---|---|---|
| 3,341,807 | 9/1967 | Lobdell | 73/610 X |
| 3,676,584 | 7/1972 | Plakos et al. | 73/614 |
| 3,887,896 | 6/1975 | Ramstedt | 367/116 |
| 3,893,449 | 7/1975 | Lee et al. | 128/661 |
| 3,940,769 | 2/1976 | Sherman et al. | 367/116 X |
| 3,969,926 | 7/1976 | Walker et al. | 73/620 |
| 4,041,441 | 8/1977 | Johnson | 367/116 X |
| 4,052,977 | 10/1977 | Kay | 128/661 |
| 4,227,417 | 10/1980 | Glenn | 128/660 X |
| 4,322,827 | 3/1982 | Weber | 367/99 |
| 4,338,948 | 7/1982 | Perez-Mendey et al. | 128/660 |
| 4,407,294 | 10/1983 | Vilkomerson | 128/660 |
| 4,412,544 | 11/1983 | Beretsky et al. | 128/660 |
| 4,658,828 | 4/1987 | Dory | 128/660 |

OTHER PUBLICATIONS

Kay, L. et al., "The Echocardiophone: A New Means for Observing Spatial Movements of the Heart", Ultrasonics, vol. 15, #3, May 1977, pp. 136–144.
Rapaport, I. et al., "A Pilot Clinical PEP Monitor", IEEE BME Trans., vol. 26, No. 6, Jun. 1979, pp. 345–349.
Bays, J. T. et al., "A Prosthetic Aid for Aiding the Blind", Ultrasonics, vol. 17, No. 1, Jan. 1979, pp. 37–42.
Zwicker, E. "Mechanisms in Hearing", Academic Press, Inc., N.Y. & London, pp. 816–817, ©1973.

Primary Examiner—Francis J. Jaworski
Attorney, Agent, or Firm—Kenyon & Kenyon

[57] ABSTRACT

A direction-finding system for localization of reflection-causing interfaces in the human body, in particular those of concretions, consists of at least one transmitter (18) emitting pulsed ultrasound and at least two ultrasound receivers (2, 3), of gate circuits (25) associated with each receiver, with variable amplifiers (26), and respective storage media (6) for ultrasonic echo signals (22, 21), and of a following device for sweep magnification (7) consisting of signal memories for readout at an adjustable clock frequency, there being provided variations of the delay differences ML and of the amplitude frequency spectra MF adjustable independently of each other. Connected downstream are devices for auditory direction finding (8, 9, 10, 15).

10 Claims, 4 Drawing Sheets

DIRECTION-FINDING SYSTEM FOR LOCALIZATION OF REFLECTION-CAUSING NTERFACES IN THE HUMAN BODY

BACKGROUND OF THE INVENTION

A. Field of Invention

This invention relates to a direction-finding system for locating reflecting interfaces, in particular of concretions in the biologic tissue of the human body. Such concretions may include, for example, gall, bladder, and kidney stones. The direction-finding system has an ultrasound pulse source, which pulses are readily transmitted through some substances, such as liquids (e.g. water) and biological tissues, and reflected by the interfaces between the liquids and other substances, and are recorded by ultrasound receivers. Additional devices transform the received ultrasonic echoes into stereophonic audible signals.

B. Description of the Prior Art

Image-forming ultrasonic display units are frequently used in the field of medicine. Other devices are known which evaluate the movement of a reflecting interface in the body (e.g. heart muscle movement of the embryo) by the Doppler effect have monophonic audio signals, as an output possibly including a threshold circuit which suppresses echo signals that are too weak, and hence not usable.

These ultrasound echo devices known in medical technology, however, permit only a non-dimensional, monophonic acoustic identification (e.g. a beep) or they indicate the output signal of a Doppler effect detector.

Problems in locating acoustically reflecting objects in the human body arise in particular in extracorporal acoustic lithotripsy wherein image-forming x-ray and ultrasonic methods are used.

As the conditions of propagation of x-rays and of sound waves in the human body are different, a congruent localization of the concretion using both systems does not result. The radiological observation of a stone furnishes shadow images usable for locating said stone, but the correlation of the stone position to the focus point of the shock wave generator is rendered difficult when the focusing dimension is small. A useful depth and lateral localization can therefore not be carried out with satisfactory certainty.

If image-forming ultrasonic methods are used for locating stones, the representations produced according to the present state of the art are interpretable only by highly specialized personnel, and reflections not produced by the stone may easily be misinterpreted. This problem is particularly prominent in distinguishing between a stone, a bone, or, a gas-containing area.

A stereophonic signal presentation in connection with position-finding problems of the blind has been proposed already in ultrasonic blind-guiding devices (DAGA '80—Fortschritte der Akustik, VDE-Verlag, Berlin 1980, pages 767 ff.). The problems of ultrasound transmissivity of biologic tissue and of water were of no importance in that field. Hence that description of a stereophonic ultrasonic direction-finding system does not teach the design of an apparatus applicable in medical technology.

Ultrasonic direction-finding systems are also known in other fields. Thus, for example for the localization of ships ultrasound pulses of short duration are emitted, the reflected echos are detected by a receiver ("transducer") and the transit time of the echo pulses is measured.

The graphic representation of sonar signals is described in U.S. Pat. Nos. 2,528,725 to 2,528,730.

SUMMARY OF THE INVENTION

The object of the present invention is the development of an ultrasonic direction-finding system useful in the medical arts for the localization of concretions in the living body which will enable the treating physician by means of acoustically perceptible signals to confirm, reject or at least question the location indicated by other known image-forming ultrasonic and radiological methods. This system must be able, therefore, to pick up and process the existence of a reflecting object within a space present at a certain distance from the ultrasound receiver, as well as the size and nature of the reflection produced by an object located there.

The assumption made here is that any normally hearing person is able to determine with sufficient precision the direction of origin of a sound. This ability is utilized by the apparatus according to the invention to simulate an audible and localizable phantom sound source with the aid of transformed ultrasonic echo signals. For two-channel stereo reproduction, a differential range of 0 to about 20 dB, is used with a time delay of 0 to about 600 microseconds for earphone reproduction and about 20 ms for loudspeaker reproduction.

The system according to the invention consists of at least one ultrasonic pulse transmitter controllable with respect to its direction of radiation, having at least two likewise orientable ultrasonic receivers. Ultrasonic transmitters are known e.g. as piezoelectric, electromagnetic, inductive, magnetostrictive transducers (transceivers) as well as explosion or spark gap transducers. The ultrasound frequencies suitable for stone detection are in the range of 100 kHz to about 5 MHz. The ultrasound pulse repetition frequency is about 5 Hz, the pulse duration being in the range of 0.5 to 100 oscillation periods.

If the object reflecting the sound is equidistant from the receivers, the reflected echo signals arrive at them simultaneously; their transit time difference is zero. The echo amplitudes are the same if the reflecting object disperses the pulses in an approximately symmetrical fashion. Due to the spheroidal shape of concretions, this is usually the case. The stereophonic reproduction equipment here produces a phantom sound source which is in the stereophonic center position.

If the object is not equidistant from the receivers, transit time differences will result in the received echo signals. A receiver located at a shorter distance from the object, detects a signal first and at a higher amplitude. The stereophonic reproduction equipment produces in response a phantom sound source which is offset from the stereophonic center position.

As the entire direction-finding field is in liquid or in biologic tissue, the resulting differential transit times of the received signals are as a rule extremely small and therefore cannot be evaluated for direction-finding directly by the human ear.

The signals picked up by the receivers are transformed into audible, stereophonic signals, which seem to be coming from a phantom sound source. According to the invention, therefore, the locating system contains devices or circuits which store the intercepted signals, determine therefrom transit time differences, amplitudes, thresholds, reflection characteristics (polarity of the reflection) and preferably also the time position of the echoes, and transform the stored signals into audible frequency ranges in analog form. It is possible to realize the devices as algorithms of computer programs rather than as electronic circuits.

Thus audible signals are produced which permit not only a lateral localization, but also by their acoustic character and their intensity an estimate of the type of reflecting object (e.g. tissue/tissue, tissue/bone or tissue concretion interfaces).

The direction-finding system according to the invention contains for each ultrasound receiver a respective gate circuit as a time window. The opening time and opening duration are chosen so that only the echo signals to be expected from an area to be examined can pass. Each gate circuit is appropriately combined with an adjustable amplifier, the gain of which can increase with the distance of the area to be examined in such a manner that on the output side a constantly high echo signal occurs if the area to be examined contains a spherical reflector.

The gate circuits are connected to a transient storage device for picking up ultrasonic echo signals with storage locations assigned to each receiver. Means are provided which subject the stored data to direct sweep magnification, as explained more fully below.

By sweep magnification it is possible to convert inaudible ultrasonic pulses into the audible frequency range in correct curve form to obtain stereophonic audio signals.

However not in all cases will a given sweep magnification scale transfer the received ultrasonic signals simultanously into the optimum mean audio frequency range of about 400 Hz to about 1 kHz and into the transit time difference range optimum for spatial perception of from 0 to about 600 microseconds. For instance, the ultrasonic pulses can contain very high frequency components (about 10 MHz) or the targeted concretions could be at a distance from the receivers such that the transformed differential echo transit time assume values which are too high (for headsets >1 ms, or for loudspeakers >10 ms) to allow stereophonic phantom-source localisation.

The direction-finding system according to the invention therefore comprises not a simple sweep magnification device for the received signals with respect to the transmission pulse synchronizing the two records, but means which adjust two transformation scales independently of each other.

One transformation scale (ML) makes it possible to select the "locating precision", that is, to freely decide which ultrasound differential echo transit time is to lead to what transit time offered to the ear in the audio reproduction. For headset reproduction the transferred transit time differences must be 0 to 600 microseconds.

Another transformation scale (MF) makes it possible to decide into what audio frequency range one wishes to place the converted ultrasound echo signals. This is of special practical importance when the tone quality of the echo is to contribute to the evaluation. It has in fact been found empirically that this makes possible a distinction between tissue echo and stone echo.

The memory reception channels carrying the reflected ultrasonic signals, triggered by the transmission pulse, are activated to receive after an inactive time following the pulse transmission. By automatic polling of the memory contents it can now easily be determined which signal arrives later and by what time period. The delay time is known with reference to the number of idle samples preceeding the arriving echo signals and this can be related to the transformation scale ML, while the signals themselves are related to the transformation scale MF. These transformations can be realized in the manner known in itself by variations of the sampling rate of the memory contents.

The ultimate goal of the audio direction finding and locating aimed at, namely to document the existence of a reflecting obstacle in a small space present at a certain distance from the ultrasound receivers, is thus possible by the mentioned sweep magnifications of the ultrasound signals storable in a time window.

A solution especially favorable for the locating consists in normalizing the two echo signals to equal levels. Thereby the audio direction-finding depends most exclusively on the differential transit time. Erroneous lateral deviations of the phantom sound source, which occur for example due to echo level differences (caused by direction-dependent reflections), are effectively suppressed.

A preferred form of the direction-finding system according to the invention contains in the ultrasound receiver section, when one transmitter is present, four receivers at the corners of an imaginary rectangle, since a receiver pair permits direction finding in one plane. Thus, in the case of square or rhombic arrangement, it becomes possible to take bearings in two planes perpendicular to each other, and hence to detect the existence of a reflecting obstacle on one axis.

The output stereo phonic system is realized in conventional manner with a two-channel arrangement. The preferred stereophonic presentation occurs via a headset which is cordlessly coupled with the signal output device via a transmitter. The connection is obtained e.g. with radio frequency means, inductively or by infrared technology.

To the stereophonic signals are added in an especially preferred variant additional identifying marks, such as tones, tone sequences, keyed tones, wobble tone, voice text outputs, which as additional information, describe the qualitative properties of the echo signals, e.g. amplitude, time position in relation to the transmission signal, transmit time difference, threshold and polarity.

Such identifying marks can also be preceptible, separately from the audio-phonic section, via visual signs (light monitors) or tacticle stimulators (vibrators) controlled by the acoustic transceiver system.

The system according to the invention permits ultrasonic detection as well as audio-signal direction-finding, in the medical field for concretions which brings about a significant increase in reliability and certainty, in cooperation with a reflector position evaluation obtainable from known image-forming ultrasonic methods. The direction-finding equipment of the invention thus helps to find the target more easily, more reliably and faster and furnishes via the acoustic, optical or tactile signal transmitters, additional useful information about the position, size and nature of the reflecting body.

DETAILED DESCRIPTION OF THE INVENTION

Figure 1:
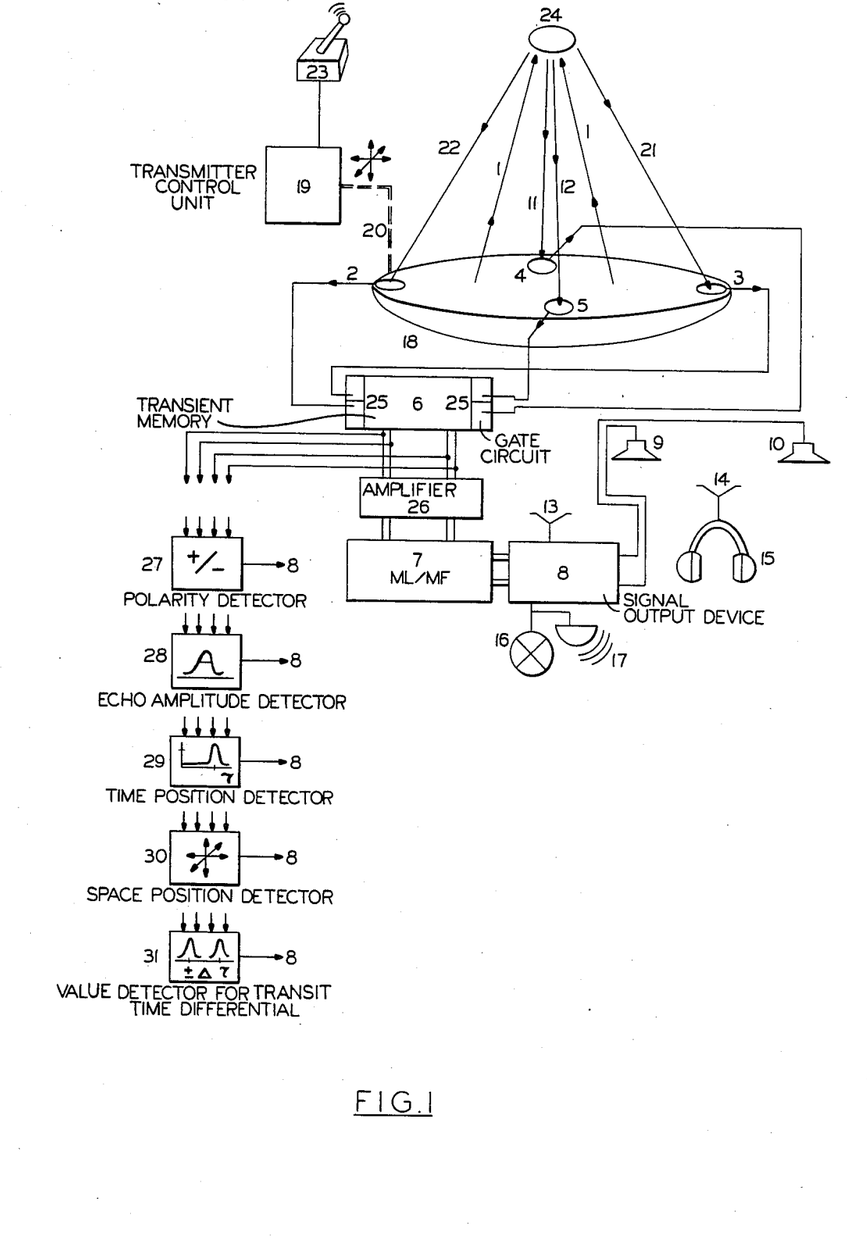
FIG. 1 shows a schematic diagram for a direction-finding system constructed in accordance with the invention.

In FIG. 1, a direction-finding system is realized with an ultrasonic transmitter 18 and a quad receiver system 2, 3, 4, 5. The stereophonic output of the receiver system is detected via a headset 15. A cordless receiver head set 15 is coupled to system 8 by radio frequency or infrared signals propagating through antennas 13 and 14.

The stereophonic signals are also sent to the loudspeakers 9 and 10 and are indicative of the location of a stone. Thus the signals provide the listener with a subjective directional indication of a phantom sound source and (upon evaluation of the tone quality of the audio echo signals) also a qualitative estimation of the reflecting object 24.

The sterophonic signals contain in this example additional identifying characteristics which are displayed via a light-emitting display 16 or an tactile stimulator 17. The latter is shown in the sketch at the bottom as a separate component, however, it is possible to generate tactile stimulations directly at the actuating element 23 controlling the position of the acoustic transceiver system.

More specifically, the stereophonic system comprises an ultrasonic transmitter 18 and four individual receivers 2, 3, 4 and 5 which are arranged respectively at the corners of a rhombus as shown. Transmitter 18 preferably comprises a hemispherical bowl of about 40 cm in diameter. The bowl is made up of a large number (up to 10000) of ceramic disks which are arranged on the bowl to generate ultrasonic waves by the application of a high-voltage electric field. Ultrasonic waves generated by the individual disks coincide at the focal point of the bowl.

Preferably, the transmitter 18 is disposed below a treatment table supporting the patient and the ultrasonic waves are transferred into the patient's body through a water-filled opening made in the table. The schematic diagram of FIG. 1 shows how the subject system is used to locate an object 24. For the purposes of this diagram, the treatment table and the patient have been omitted, however it should be understood that object 24 is preferably a concretion produced within a patient's body.

If object 24 reflecting emitted ultrasonic pulses 1, which is equidistant from these receivers 2-5 the reflected echo signals 11, 12 and 21, 22, arrive at the same time to the receivers 4, 5 and 3, 2 respectively. Hence the transit time difference is zero and the echo amplitudes are practically identical if the object reflects approximately symmetrically.

If the object 24 is at a different distance from the receivers, there result transit time differences in the received echo ultrasound signals 11 and 12 or respectively 21 and 22. The receivers closest to the object detect the signals earlier and at a higher amplitude.

The received ultrasound echo signals 11, 12 and 21, 22 are windowed by four separate gate circuits 25, are stored in the four-channel transient memory 6, and supplied to the sweep magnifier 7 via the amplifier 26.

For separate, independent variation of the transit times via the transformation scale ML and of the audio frequency range via the transformation scale MF, the memory contents are retrieved from memory 6 singly and, allowing for a delay after the transmitting pulse, it is determined which signal arrives later and by what time period. The delay time is now known on the basis of the different number of idle samples preceeding the echo signals and can be detected through the transformation scale ML, while the signals themselves are interpreted with the transformation scale MF.

After these values are adjusted, it is possible by way of the control 23, control unit 19 and the connection 20 to the servomotors (not shown) to move the entire transducer system 18 in three directions and to pivot it back and forth until, via the display unit, the exact position and the nature of the reflecting object 24 have been determined.

Selectively singly or in combination with one another, the outputs of the transient memory 6 can be linked with detectors for determining the polarity (hard/soft reflection) (27), the echo amplitudes (28), the time position (29) of the echoes 11, 12, 21, 22 with respect to the transmission signal 1, the space position (30) of the concretion 24, as well as the value and/or sign of the transit time differences (31). These detectors control one or more signal output devices 8, which process the data and provide signals to loudspeakers 9, 10, headset 15, display 16, or tactile stimulator 17.

Figure 2:
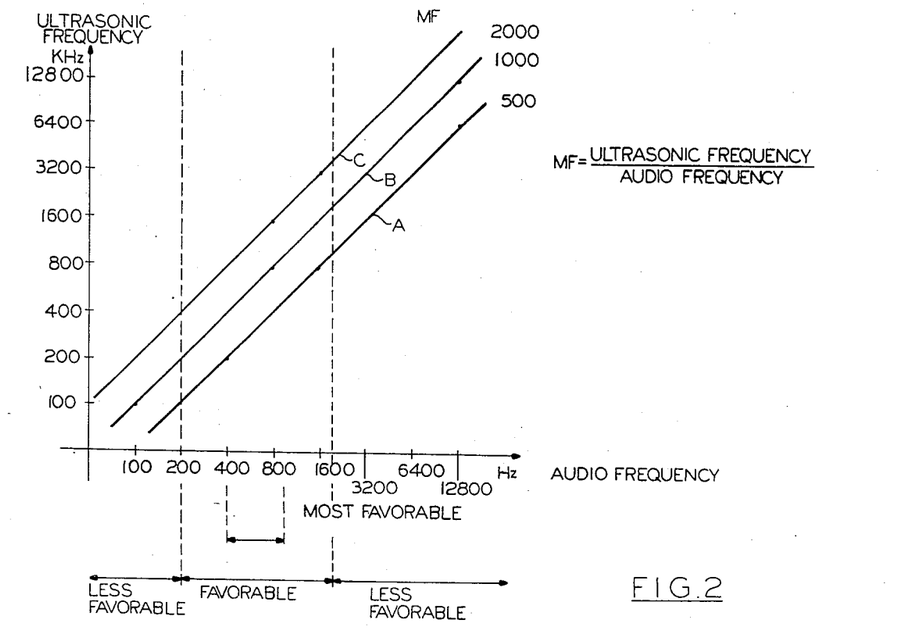
FIG. 2 shows a graph for various values of the constant MF.

As shown in FIG. 2, preferably transformation MF is linear whereby the ratio between the ultrasonic frequency US of the waves produced by transmitter 18 and the frequency of the audisounds produced by device 8 is a constant MF. In FIG. 2, curves A, B and C correspond to constant MF having values of 500, 1000 and 2000 respectively. It has been found that the system operates best if the audio signals of device 8 are selected in the range of 200 to 1600 HZ, and preferably in the range of 400 to 800 HZ. Once a frequency for the audio signals, and the constant MF is selected, the frequency of the ultrasonic waves may be found from FIG. 2. Audio signals above 1600 Hz or below 200 HZ are less favorable.

Figure 3:
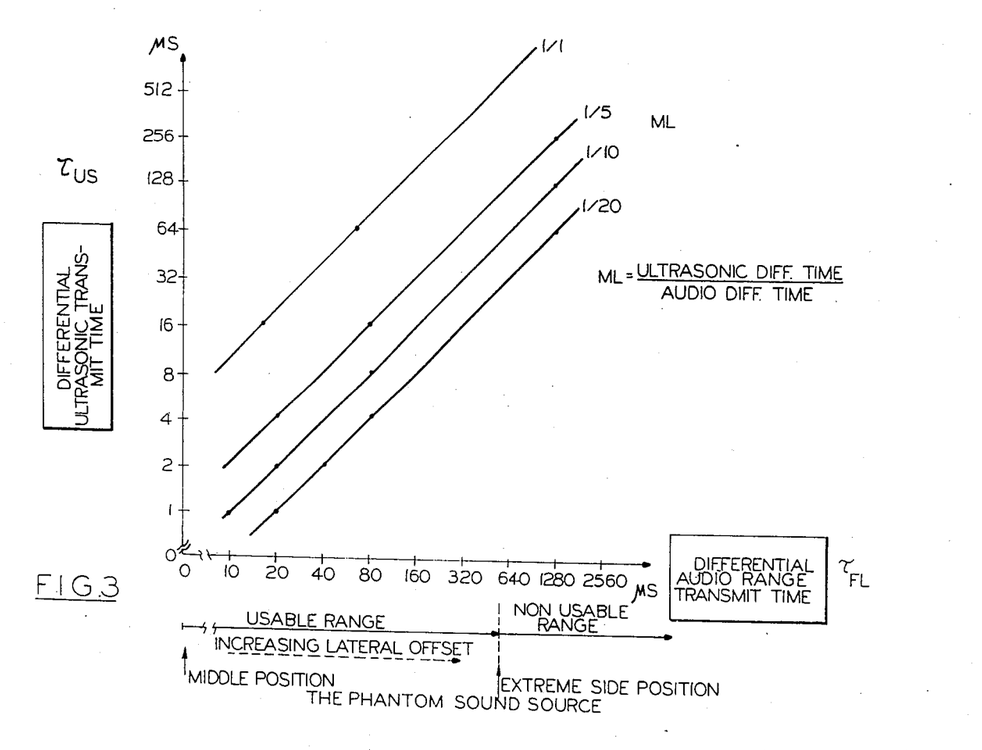
FIG. 3 shows a log/log graph of four different transforming ML values.
Figure 4:
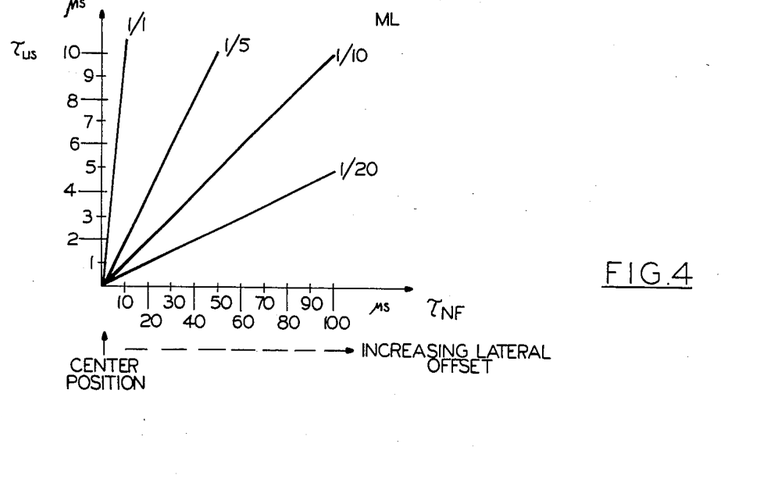
FIG. 4 shows a linear/linear graph of four different transforming ML values.

FIGS. 3 and 4 show four ways for transforming the differential transit times of the ultrasonic echoes (the ordinate axis) to corresponding differential transit times for audio signals. In FIG. 3 it is indicated that for earphone reproduction, the audio signals transit time must be in the range of 0–640 microseconds. Different transformation scales ML result in different "precision" in the quality of the audio signals.

Figures 5A, 5B:
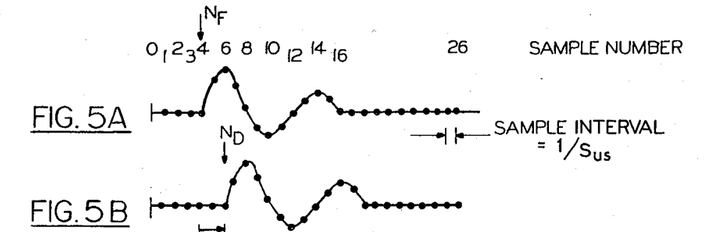
FIGS. 5(a), 5(b), 5(c), 5(d), 5(e) and 5(f) show various waveforms developed within the device of FIG. 1.
Figure 5C:
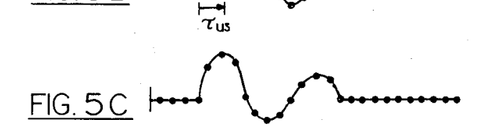
Figure 5D:
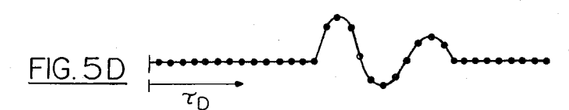
Figures 5E, 5F:
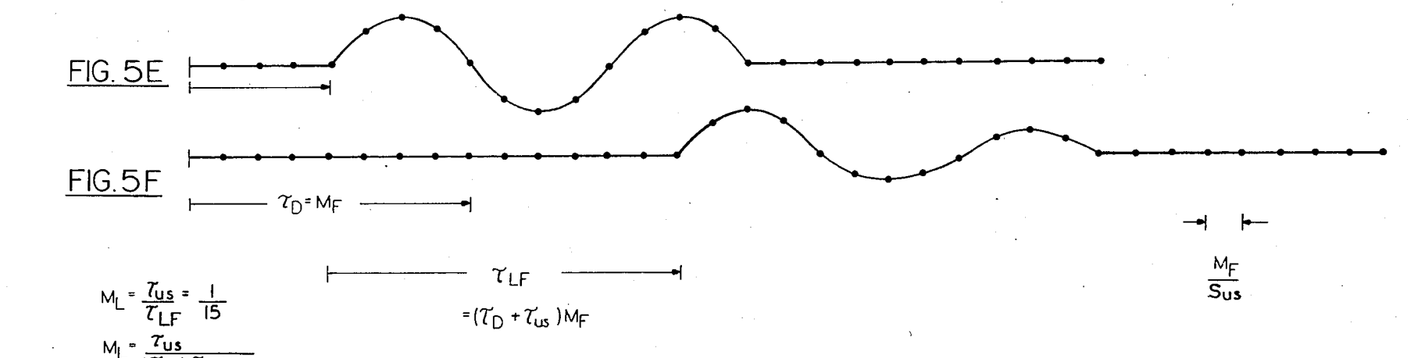
Figure 6:
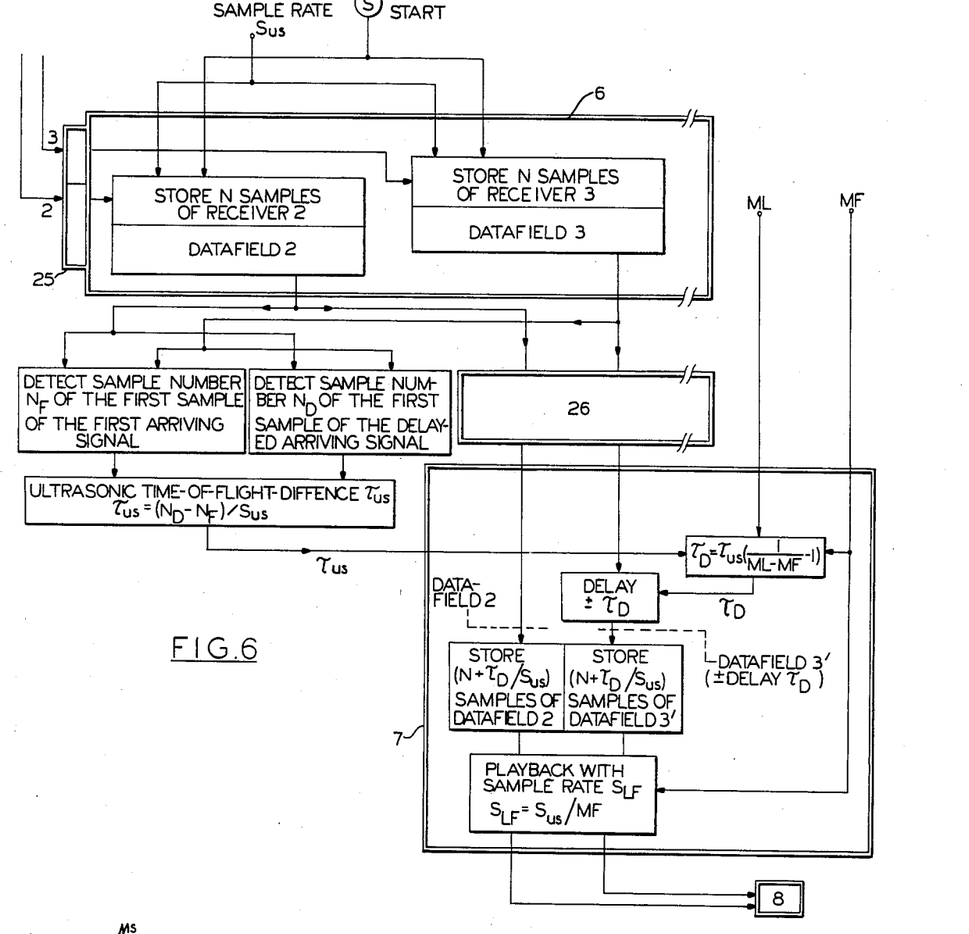
FIG. 6 shows in block diagram the signal processing required to obtain the waveforms of FIG. 5.

The signal processing required to transform the signals in the ultrasonic range into signals in the audio range shall now be described with reference to FIGS. 5 and 6. FIG. 5 illustrate various wave forms within the system as a function of time while FIG. 6 shows how these waveforms are derived.

Initially, transmitter 18 of FIG. 1 generates a burst of ultrasonic waves. These waves may be in the frequency range of 100 KHZ to 10 MHZ. A device using a frequency of 480 KHZ was operated successfully. The burst is relatively short. For example the burst may be in the range of 1.5–2 periods. The response from receivers 2 and 3 are fed respectively to memory 6 through two gate circuits 25. (FIG. 6). Within memory 6 these analog signals are sampled at a sampling frequency of $S_{us}$ and stored to form data fields 2 and 3 respectively. The sampling rate is dependent on the frequency of the waves produced by generator 1. As is well known from communication theory, this frequency must be at least twice the frequency of the ultrasonic waves. Thus, $S_{us}$ may be in the range of 200 KHz–20 MHz. In order to insure the accuracy of the results, the sampling rate could be increased to a range of 10–100 MHz corresponding to a sampling interval of (signal to $1/S_{us}$) of 0.1 microsec to 10 nanosec. A short sampling time interval insures that the differential transit time between two received waves is detected accurately.

Typically, a differential transit time of up to $\pm 20$ microsec, may be stored in memory, which permits at 100 MHZ sampling rate the detection of an object which is of $\pm 3$ cm from the focal point. If the sampling rate is reduced by a factor of two, the detector range of the device is from $\pm 0.06$ mm to $\pm 6$ cm corresponding to a differential time delay between the echo signals of 40 nanosec to 40 microseconds.

The wave shapes of FIG. 5 were obtained by generating an ultrasonic wave of 480 KHz for 1.5 time periods. After delay at $t=0$ the gate circuits (25) are opened. The signal bounces off concretion 24 and is detected by receiver (2) four time intervals later (FIG. 5a) and by receiver (3) six time intervals later (FIG. 5b). Therefore, the differential time delay between the two signals is two sampling intervals.

As shown in FIG. 6, the intervals $N_F$ and $N_D$ indicative of the detector of the echo signals by receivers 2 and 3 respectively are used to calculate the differential time delay from the formula:

$$t_{us} = (N_D - N_F)/S_{us}$$

This time delay tus (separating the ultrasonic time delay) is used by the sweep magnifier 7 to generate a corresponding audio time delay $t_d$ from the formula $$t_d = t_{us}(1/ML \cdot MF - 1)$$

Datafields 2 and 3 are amplified by amplifier 26. Datafield 2 remains essentially unchanged as indicated by FIG. 5(c). Datafield 3 is delayed by $t_d$ to generate a datafield 3', as shown in FIG. 5(d) wherein $t_d = 8$ sampling intervals. $N + t_d/U_{us}$ samples of datafields 2 and 3' are stored (N being the number of samples for the wave in FIG. 5(a), i.e. 27). These values are played backed at a much slower rate $S_{LF} = S_{us}/MF$ thereby effectively expanding the two waves in time as shown in FIGS. 5(e) and 5(f) respectively. The differential time delay between these expanded waves is given by $$T_{LF} = (t_d + t_{us})MF \text{ or}$$

$$T_{LF} = [t_{us}(1/ML \cdot MF - 1) + t_{us}]MF \text{ or}$$

$$T_{LF} = t_{us}/ML$$

Thus the delay $T_{LF}$ is independent of MF, and therefore the two variables ML and MF can be chosen arbitrarily.

It should be understood that the waveshapes of FIGS. 5(a)–(f) and the numerical values given above have been described or given for illustrative purposes only and are not to be interpreted as limitations on the claims. The values $N_D$, $N_F$ and $t_{us}$ are preferably determined and calculated as follows:

$N_F$ and $N_D$ by the time position detector (29),
$t_{us}$ by the transit time detector (31),
$t_d$ by the sweep magnifier (7), shown in FIG. 1.

Obviously, numerous modifications may be made to the invention without departing from its scope as defined in the appended claims.

what is claimed is:

1. A system for localizing reflection-causing interfaces, particularly concretions, in the human body, the system comprising:
   ultrasound pulse transmitter means for transmitting ultrasound pulses in a plurality of directions;
   a plurality of ultrasound receiver means for receiving the transmitted pulses;
   gate circuit means coupled to the receiver means for accepting the received ultrasound pulses, the gate circuit means only accepting pulses within a preset time period;
   amplifier means coupled to the gate circuit means for amplifying the accepted ultrasound pulses;
   storage means coupled to the amplifier means for storing the amplified ultrasound pulses;
   MF transformation means coupled to the storage means for transforming the amplified ultrasound pulses into amplified audio pulses within a preset audio frequency range;
   ML transformation means coupled to the storage means and the MF transformation means, the ML means measuring the time delay between the received ultrasonic pulses, calculating an appropriate audio frequency time delay, and applying the time delay to the MF audio pulses to produce time delayed audio pulses;
   stereophonic audio output means coupled to said ML transformation means and MF transformation means for outputting a stereophonic audio signal, the presence of a time delay in the audio signals skewing the perceived location of the sound source to an appropriate side.

2. The system of claim 1 wherein the transmitter means and the receiver means are formed on the same body.

3. The system of claim 1 further comprising visual indicator means and tactile indicator means coupled to the ML and MF transformation means for outputting the audio pulses received from the ML and MF transformation means as a visual signal and a tactile signal.

4. The system of claim 1 wherein a single ultrasound pulse transmitter means and four ultrasound receiver means are used, each receiver being located in the corner of an imaginary rhombus.

5. The system of claim 1 further comprising polarity detector means coupled to the amplifier means for determining the polarity of the received ultrasound pulses in comparison with the transmitted ultrasonic pulse and outputting said polarity.

6. The system of claim 1 wherein the stereophonic output means comprises a cordless stereo headset.

7. The system of claim 1 further comprising signal amplitude means coupled to the amplifier means for determining and outputting the amplitude of the received ultrasonic pulses, time position detector means coupled to the amplifier means for determining and outputting the time period between the transmission and reception of the ultrasound pulses, spacial locator means coupled to the amplifier means for determining and outputting the location of the concretion, and transit time difference means coupled to the amplifier means for determining and outputting the value and sign of the transit time differences between the various receiver means.

8. A system for detecting and localizing a concretion in the human body, the system comprising:
- ultrasonic pulse transmitter means for transmitting ultrasonic pulses;
- a plurality of ultrasonic pulse receiver means for receiving ultrasonic pulses after reflection from the concretion;
- gate circuit means coupled to the receiver means for determining if the receiver means receive the reflected ultrasonic pulses simultaneously and, if reception is not simultaneous, for determining which receiver means received the pulse first and for measuring what the length of delay between the respective reception of the pulses by the receiver means was;
- MF transformation means coupled to the gate circuit means for transforming the received ultrasonic pulses into audio signals of a preset frequency range;
- ML transformation means coupled to both the gate circuit means and the MF transformation means for applying the measured time delay between reception of the pulses at the respective receiver means to the audio signals produced by the MF means to produce a stereophonic audio signal having a right and left channel, the time delay skewing the signal to the right or left channel, as appropriate; and
- stereophonic output means coupled to the ML and MF transformation means for outputting the stereophonic audio signal, the output being skewed to the right and left channel as determined by the measured time delay.

9. The system of claim 8, wherein both ML and MF transformation means comprise a single integrated circuit means.

10. The system of claim 8 wherein the stereophonic audio output appears to emanate from a phantom signal source whose location is skewed in the direction of the receiver means which received the ultrasonic pulse first.

* * * * *

UNITED STATES PATENT AND TRADEMARK OFFICE
CERTIFICATE OF CORRECTION

PATENT NO. : 4,805,622

DATED : February 21, 1989

INVENTOR(S) : Rainer Riedlinger, et al.

Page 1 of 5

It is certified that error appears in the above-identified patent and that said Letters Patent is hereby corrected as shown below:

Column 1, (Abstract Page), line 3, "NTERFACES" should read --INTERFACES--.

Column 1, (Abstract Page), second to last, "Perez-Mendey" should read --Perez-Mendez--.

Column 1, line 4, "NTERFACES" should read --INTERFACES--.

Column 1, line 46, "with satisfactory certainty" should read --with certainty--.

Column 1, line 66, "Thus, for example" should read --For example,--.

Column 2, (Abstract Page), line 25, "7." should read --7--.

Column 2, line 26, "dB,' is" should read --dB is--.

UNITED STATES PATENT AND TRADEMARK OFFICE
CERTIFICATE OF CORRECTION

PATENT NO. : 4,805,622
DATED : February 21, 1989
INVENTOR(S) : Rainer Riedlinger, et al.

It is certified that error appears in the above-identified patent and that said Letters Patent is hereby corrected as shown below:

Column 2, line 53, "object, detects" should read --object detects--.

Column 3, line 31, "However not" should read --However, not--.

Column 3, line 32, "transfer" should read --transform--.

Column 3, line 33, "simultanously" should read --simultaneously--.

Column 3, line 40, "transit" should read --transient--.

Column 3, line 43, "localisation" should read --localization--.

Column 4, line 31, "stereo phonic" should read --stereophonic--.

Column 4, line 46, "audio-phonic" should read --audiophonic--.

Column 4, line 47, "tacticle" should read --tactile--.

UNITED STATES PATENT AND TRADEMARK OFFICE
CERTIFICATE OF CORRECTION

PATENT NO. : 4,805,622
DATED : February 21, 1989
INVENTOR(S) : Rainer Riedlinger, et al.

It is certified that error appears in the above-identified patent and that said Letters Patent is hereby corrected as shown below:

Column 4, line 51, "concretions which" should read --concretions, which--.

Column 5, line 14, "head set" should read --headset--.

Column 5, line 26, "an" should read --a--.

Column 5, line 28, "component, however" should read --component; however--.

Column 5, line 38, "10000" should read --10,000--.

Column 5, line 49, "omitted," should read --omitted;--.

Column 5, line 50, "however it" should read --however, it--.

Column 5, line 55, "22, arrive" should read --22 arrive--.

Column 5, line 56, "2 respectively" should read --2, respectively--.

UNITED STATES PATENT AND TRADEMARK OFFICE
CERTIFICATE OF CORRECTION

PATENT NO. : 4,805,622

DATED : February 21, 1989

INVENTOR(S) : Rainer Riedlinger, et al.

It is certified that error appears in the above-identified patent and that said Letters Patent is hereby corrected as shown below:

Column 5, line 62, "or respec-" should read --or, respec--.

Column 5, line 63, "tively 21" should read --tively, 21--.

Column 5, line 67, "and" should read --and are--.

Column 6, line 36, "2000 respectively" should read --2000, respectively--.

Column 6, lines 38 and 39, "HZ" should read --Hz--.

Column 6, line 40, "MF is" should read --MF, is--.

Column 6, line 42, "HZ" should read --Hz--.

Column 6, line 48, "signals" should read --signal--.

Column 6, line 50, " "precision" " should read --precision--.

Column 7, line 68, "(31)," should read --(31), and--.

UNITED STATES PATENT AND TRADEMARK OFFICE
CERTIFICATE OF CORRECTION

PATENT NO. : 4,805,622

DATED : February 21, 1989

INVENTOR(S) : Rainer Riedlinger, et al.

Page 5 of 5

It is certified that error appears in the above-identified patent and that said Letters Patent is hereby corrected as shown below:

Column 8, line 5, "what" should read --What--.

Column 8, line 31, "pulses;" should read --pulses; and--.

Column 10, line 14, "8, wherein" should read --8 wherein--.

Signed and Sealed this

Twenty-third Day of October, 1990

Attest:

HARRY F. MANBECK, JR.

*Attesting Officer*

*Commissioner of Patents and Trademarks*